United States Patent
Podolski et al.

(10) Patent No.: US 9,981,906 B2
(45) Date of Patent: May 29, 2018

(54) TRANS-CLOMIPHENE METABOLITES AND USES THEREOF

(75) Inventors: Joseph S. Podolski, The Woodlands, TX (US); Ronald D. Wiehle, Houston, TX (US)

(73) Assignee: Repros Therapeutics Inc., The Woodlands, TX (US)

( * ) Notice: Subject to any disclaimer, the term of this patent is extended or adjusted under 35 U.S.C. 154(b) by 141 days.

(21) Appl. No.: 14/236,868

(22) PCT Filed: Aug. 3, 2012

(86) PCT No.: PCT/US2012/049451
§ 371 (c)(1),
(2), (4) Date: Feb. 3, 2014

(87) PCT Pub. No.: WO2013/020017
PCT Pub. Date: Feb. 7, 2013

(65) Prior Publication Data
US 2014/0163114 A1  Jun. 12, 2014

Related U.S. Application Data

(60) Provisional application No. 61/515,278, filed on Aug. 4, 2011.

(51) Int. Cl.
*C07C 217/18* (2006.01)

(52) U.S. Cl.
CPC .................................. *C07C 217/18* (2013.01)

(58) Field of Classification Search
None
See application file for complete search history.

(56) References Cited

U.S. PATENT DOCUMENTS

| | | | |
|---|---|---|---|
| 2,914,563 A | 11/1959 | Allen et al. | |
| 3,848,030 A | 11/1974 | Viterbo et al. | |
| 4,061,733 A | 12/1977 | Gunnikar | |
| 4,729,999 A | 3/1988 | Young | |
| 4,820,736 A * | 4/1989 | Jensen | A61K 31/135 514/651 |
| 4,894,373 A | 1/1990 | Young | |

(Continued)

FOREIGN PATENT DOCUMENTS

| | | |
|---|---|---|
| AU | 2001261684 | 12/2001 |
| CN | 103351304 A | 10/2013 |

(Continued)

OTHER PUBLICATIONS

Ruenitz et al. Cancer Research 47, 4015-4019, Aug. 1, 1987.*

(Continued)

*Primary Examiner* — Clinton A Brooks
(74) *Attorney, Agent, or Firm* — Morgan Lewis & Bockius LLP

(57) ABSTRACT

The present invention relates to substantially pure metabolites of irara-clomiphene. The invention is also directed to pharmaceutical compositions comprising these metabolites and their use in treating disorders including secondary hypogonadism, type 2 diabetes, elevated cholesterol, elevated triglycerides, wasting, lipodystrophy, female and male infertility, benign prostate hypertrophy, prostate cancer, breast cancer, ovarian cancer and endometrial cancer.

1 Claim, 2 Drawing Sheets

(56) References Cited

U.S. PATENT DOCUMENTS

| | | | |
|---|---|---|---|
| 5,681,863 | A | 10/1997 | Bitonti et al. |
| 5,728,688 | A | 3/1998 | Labrie |
| 5,861,389 | A | 1/1999 | Radlmaier |
| 6,017,964 | A | 1/2000 | MacLean et al. |
| 6,096,338 | A | 8/2000 | Lacy |
| 6,126,969 | A | 10/2000 | Shah |
| 6,129,933 | A | 10/2000 | Oshlack |
| 6,143,353 | A | 11/2000 | Oshlack |
| 6,190,591 | B1 | 2/2001 | Van Lengerich |
| 6,221,399 | B1 | 4/2001 | Rolfes |
| 6,248,363 | B1 | 6/2001 | Patel |
| 6,291,505 | B1 | 9/2001 | Heubner et al. |
| 6,342,250 | B1 | 1/2002 | Masters |
| 6,391,920 | B1 | 5/2002 | Fisch |
| 6,511,986 | B2 | 1/2003 | Zhang et al. |
| 6,583,129 | B1 | 6/2003 | Mazer et al. |
| 6,600,010 | B2 | 7/2003 | Mao et al. |
| 6,638,528 | B1 | 10/2003 | Kanios |
| 6,645,974 | B2 | 11/2003 | Hutchinson et al. |
| 6,653,297 | B1 | 11/2003 | Hodgen |
| 6,685,957 | B1 | 2/2004 | Bezemer et al. |
| 6,743,448 | B2 | 6/2004 | Kryger |
| 7,067,557 | B2 | 6/2006 | Fisch |
| 7,105,679 | B2 | 9/2006 | Kanojia et al. |
| 7,354,581 | B2 | 4/2008 | Cedarbaum et al. |
| 7,799,782 | B2 | 9/2010 | Munson et al. |
| 8,247,456 | B2 | 8/2012 | Podolski |
| 8,377,991 | B2 | 2/2013 | Van As |
| 2002/0120012 | A1 | 8/2002 | Fisch |
| 2002/0183296 | A1 | 12/2002 | Dudley et al. |
| 2003/0040510 | A1 | 2/2003 | Labrie |
| 2004/0097597 | A1 | 5/2004 | Podolski et al. |
| 2004/0171697 | A1 | 9/2004 | Podolski et al. |
| 2004/0220154 | A1 | 11/2004 | Kryger |
| 2004/0241224 | A1 | 12/2004 | Podolski et al. |
| 2005/0042268 | A1 | 2/2005 | Aschkenasy et al. |
| 2005/0171073 | A1 | 8/2005 | Steiner et al. |
| 2006/0269611 | A1 | 11/2006 | Steiner et al. |
| 2006/0293294 | A1 | 12/2006 | Blom et al. |
| 2007/0004626 | A1 | 1/2007 | Masuda et al. |
| 2007/0101166 | A1 | 5/2007 | Boyum et al. |
| 2007/0202166 | A1 | 8/2007 | Heuer et al. |
| 2009/0036415 | A1 | 2/2009 | Rubin et al. |
| 2009/0099265 | A1 | 4/2009 | Van As |
| 2009/0215906 | A1 | 8/2009 | Podolski |
| 2010/0054248 | A1 | 3/2010 | Gutierrez |
| 2010/0111901 | A1 | 5/2010 | Gant et al. |
| 2010/0144687 | A1 | 6/2010 | Glaser |

FOREIGN PATENT DOCUMENTS

| | | |
|---|---|---|
| EP | 0206021 A | 8/1988 |
| EP | 0430388 A2 | 6/1991 |
| EP | 0888775 A2 | 7/1999 |
| EP | 1090639 A2 | 4/2001 |
| EP | 1829534 A1 | 3/2006 |
| JP | 4-312522 | 11/1992 |
| JP | 2005-520779 | 7/2005 |
| WO | WO 95/35093 | 12/1995 |
| WO | WO 00/005954 | 2/2000 |
| WO | WO 01/34117 A1 | 5/2001 |
| WO | WO 01/91744 A1 | 12/2001 |
| WO | WO 02/30355 | 4/2002 |
| WO | WO 03/005954 A2 | 1/2003 |
| WO | WO 03/005954 A3 | 1/2003 |
| WO | WO 03/026568 A2 | 4/2003 |
| WO | WO 03/072092 | 9/2003 |
| WO | 2006/019916 | 2/2006 |
| WO | WO 06/019916 | 2/2006 |
| WO | WO 06/084153 | 8/2006 |
| WO | WO 06/102232 | 9/2006 |
| WO | WO 07/019165 | 2/2007 |
| WO | WO 08/005469 | 1/2008 |
| WO | WO 09/051908 | 4/2009 |
| WO | WO 10/054248 | 5/2010 |
| WO | WO 13/020017 | 2/2013 |
| WO | WO 13/020215 | 2/2013 |
| WO | WO 13/130832 | 9/2013 |
| WO | 2014031177 A1 | 2/2014 |

OTHER PUBLICATIONS

Ito et al. in Cancer Science 94(1), 3-8 (2003).*

U.S. Appl. No. 14/095,494, filed Dec. 3, 2013, which is a continuation of U.S. Appl. No. 12/838,036.

Ganchev, B., et al., "Quantification of Clomiphene Mtabolite Isomers in Human Plasma by Rapid-Resoslution Liquid Chromatography-Electrospray Ionization-Tandem Mass Spectrometry," Anal. Bioannal. Chem., vol. 400, No. 10, pp. 3429-3441 (2011).

Baumann, R. Jeffrey, et al., "Clomiphene Analogs with Activity In Vitro and In Vivo Against Human Breast Cancer Cells," Biochemical Pharmacology, vol. 55, pp. 841-851 (1998).

Ruenitz, Peter, et al., "Phenolic Metabolites of Clomiphene: [(E,Z)-2[4-(1,2-Diphenyl-2-chlorovinyl)phenoxy]ethyl] diethylamine. Preparation, Electrophilicity, and Effects in MCF 7 Breast Cancer Cells," J. Med. Chem., vol. 32, pp. 192-197 (1989).

ACCE Clinical Practice Guidelines for the Evaluation and Treatment of Hypogonadism in Adult Male Patients (Nov. 1996).

Adamopoulos, et al., Fertility and Sterility, vol. 80, No. 4, pp. 914-920 (Oct. 2003).

Adashi, Eli, Y., "Clomiphene Citrate: The Case for a Monoisomeric Preparation," Bailliere's Clinical Obstetrics and Bynaecology, vol. 7, No. 2, pp. 331-347 (Jun. 1993).

Agarwal, et al., "Male Sexual Dysfunction After Stroke," J Assoc. Physicians India, vol. 37, No. 8, pp. 505-507 (Aug. 1989).

Anonymous: "Zonagen Presents Data for Androxal in the Treatment of Hypogonadal Men and Data for Progenta as a Potential New Approach in the Treatment of Breast Cancer," News Release, The Healthcare Sales & Marketing Network, XP-002352050, Sep. 2, 2004.

Bandhauer, K., et al., "Varicocele: Spermiogram, Testicular Biopsy, Plasma Testosterone. Results of Therapy," Urologe—Ausgabe A, vol. 16, No. 3, pp. 154-157 (May 1977).

Banner, A., et al., "Emerging Role of Corticosteroids in Chronic Obstructive Pulmonary Disease," The Lancet, vol. 354, pp. 440-441 (Aug. 7, 1999).

Barg, P., et al., "Male Factor: Clinical Evaluation of the Semen Analysis," Infert. Reprod. Med. Clin. North Amer., vol. 2, pp. 333-340 (Apr. 1991).

Bartsch, G., "The Effect of Antiestrogen, Antiandrogen, and the Prolactin Inhibitor 2 Bromo-'alpha!-ergocriptine on the Stromal Tissue of Human Benign Prostatic Hyperplasia. Correlation of Sterological Data and Plasma Hormones," Database Embase; Elsevier Science Publishers, Amsterdam, NL, Jan. 1981, vol. 18, No. 4, pp. 308-312.

Baumann, R. Jeffrey, et al., "Clomiphene Analogs with Activity In Vitro and In Vivo Against Human Breast Cancer Cells," Biochemical Pharmacology, vol. 55, pp. 841-851 (Mar. 1, 1998).

Ben-Jonathan, N., et al., "Dopamine as a Prolactin (PRL) Inhibitor," Endocr. Rev. 22(6), pp. 724-763 (Dec. 2001).

Bitonti, A., J., et al., "Antiproliferative Activity of Enclomiphene and Analogs with Extended Diethylaminoalkoxy Sidechains Against Human Breast Cancer Cells In Vitro and Human Tumor Xenografts in Nude Mice," Proceedings of the Annual Meeting of the American Association for Cancer Research, vol. 35, pp. 267 (Apr. 13, 1994).

Bhasin, S., et al., "Testosterone Therapy in Adult Men with Androgen Deficiency Syndromes: An Endocrine So Society Clinical Practice Guideline," J. Clin Endocrin, Metabol., vol. 91, pp. 1995-2010 (Jun. 2006).

Borghouts, L., et al., "Exercise and Insulin Sensitivity: a review" Int J Sports Med, vol. 21, No. 1, pp. 1-12 (Jan. 2000) Abstract.

Boyanov, M., et al., "Testosterone Supplementation in Men with Type 2 Diabetes, Visceral Obesity and partial Androgen Deficiency," The Aging Male, vol. 6, pp. 1-7 (Feb. 14, 2003).

Breznik, R., et al., "Effectiveness of Antiestrogens in Infertile Men, "Arch. Androl., vol. 31(1), pp. 43-48 (Jan. 1, 1993).

(56) References Cited

OTHER PUBLICATIONS

Brody, J., "Sperm Found Especially Vulnerable to Environment," The New York Times, Mar. 10, 1981.
Broulik, P.D., "Tamoxifen Prevents Bone Loss in Castrated Male Mice," Hormone and Metabolic Research, Thieme-Stratton, Stuttgart, DE, vol. 32, No. 5, pp. 181-184 (Feb. 2000) XP009041862.
Bryant, H. U., "The Pharmacology of Selective Estrogen Receptor Modulators," Principles of Bone Biology (3rd Edition), vol. 1, Chapter 41, pp. 887-919 (2008) Abstract.
Burghardt, R., et al., "Gap Junction Modulation in Rat Uterus. III. Structure-Activity Relationships of Estrogen Receptor-Binding Ligands on Myometrial and Serosal Cells," Biol. Reprod. vol. 36, No. 3, pp. 741-751 (Apr. 1, 1987).
Casaburi, R., et al., "Effects of Testosterone and Resistance Training in Men with Chronic Obstructive Pulmonary Disease," American Journal of Respiratory and Critical Care Medicine, vol. 170, pp. 870-878 (Jul. 15, 2004).
Chakraborty, P. et al., "Effects of Long-Term Treatment With Estradiol or Clomiphene Citrate on Bone Maintenance, and Pituitary and Uterine Weights in Ovariectomized Rats," J. Steroid Biochem. Molec. Biol., vol. 40, No. 4-6, pp. 725-729 (Dec. 31, 1991).
Chander, S., et al., "The Biological Evaluation of Novel Antioestrogens for the Treatment of Breast Cancer," Critical Reviews in Oncology, vol. 15, No. 3, pp. 243-269 (Dec. 1, 1993).
Chang, Ching-Fong, et al., "Stimulation of Ovulation in Ayu Plecoglossus-altivelis by Treatment with Antiestrogens and Luteinizing Hormone-Releasing Hormone Analog," Aquaculture, vol. 101, Nos. 3-4, pp. 329-336 (Feb. 15, 1992).
Check, J., et al., "Empirical Therapy of the Male with Clomiphene in Couples with Unexplained Infertility" Int. Journal Fertil., vol. 34(2), pp. 120-122 (Dec. 1988).
Clark, James H., et al., "Agonistic and Antagonistic Effects of Clomiphene Citrate and Its Isomers," Biology of Reproduction, vol. 25, pp. 667-672 (1981).
Clomid Information Sheet (available online at http//clomid.us) accessed Mar. 2, 2011.
Cooper, A., et al., "The Effects of Clomiphene in Impotence a Clinical and Endocrine Study," British Journal of Psychiatry, vol. 120, pp. 327-330 (Mar. 1972).
Cunningham, G., et al., "Testosterone Replacement Therapy and Sleep-Related Erections in Hypogonadal Men," J. Clin. Endocrinol. Metab., vol. 70, No. 3, pp. 792-797 (Mar. 1990).
Dangprasit, P., et al., "Development of Diclofenac Sodium Controlled Release Solid Dispersions by Spray Drying Using Optimization Strategy I. Powder Formulation," Drug. Devel. and Industrial Pharm. 21(20), pp. 2323-2337 (Jan. 1, 1995).
Davidson, J., et al., "Effects of Androgen on Sexual Behavior in Hypogonadal Men," J. Clin. Endocrinol. Metab., vol. 48, No. 6, pp. 955-958 (Jun. 1979).
Debigare, R., et al., "Peripheral Muscle Wasting in Chronic Obstructive Pulmonary Disease," American Journal of Respiratory and Critical Care Medicine, vol. 164, pp. 1712-1717 (Nov. 1, 2001).
de Boer, et al., "Letrozole normalizes serum testosterone in severely obese men with hypogonadotropic hypogonadism" Diabetes, Obesity and Metabolism, vol. 7, No. 3, pp. 211-215 (May 1, 2005).
de Leo, V., et al., "Clomiphene Citrate Increases Insulin-Like Growth Factor Binding Protein-1 and Reduces Insulin-Like Growth Factor-I Without Correcting Insulin Resistance Associated with Polycystic Ovarian Syndrome," Human Reproduction, vol. 15, No. 11, pp. 2302-2305 (Nov. 1, 2000).
Drew, A., "Letter: Possible Teratogenic Effect of Clomiphene," Developmental Medicine and Child Neurology, vol. 16, No. 2, pp. 276 (1974).
Dunn, S., et. al., "Insulin-like Growth Factor 1 (IGF-1) Alters Drug Sensitivity of HBL100 Human Breast Cancer Cells by Inhibition of Apoptosis Induced by Diverse Anticancer Drugs," Cancer Research, vol. 57, pp. 2687-2693 (Jul. 1, 1997).
Eastell, R., "Effect on Aromatase Inhibitor on BMD and Bone Turnover Markers: 2-Year Results of the Anastrozole, Tamoxifen, Alone or in Combination (ATAC) Trial (18233230)," Journal of Bone and Mineral Research, vol. 21, No. 8, pp. 1215-1223 (May 22, 2006).
Editions Du Vidal Ed—Editions Du Vidal: Vidal 1997; Dictionnaire Vidal 1997, Paris, FR, p. 1161 XP002150196.
Eil, C., "Ketoconazole Binds to the Human Androgen Receptor," Hormone and Metabolic Research, vol. 24, No. 8, pp. 367-370 (Aug. 1992).
Elanjian, S., "Clomiphene for Male Infertility," Journal of Pharmacy Technology, vol. 12, No. 3, pp. 102-104 (May 1, 1996).
EP Supplementary Search Report of EP 02748104 dated Jun. 24, 2005.
EP Supplementary Search Report of EP 06720243 dated Aug. 6, 2008.
EP Supplementary Search Report of EP 06738985 dated Aug. 15, 2008.
EP Supplementary Search Report of EP 06800648 dated Jul. 21, 2008.
EP Extended Search Report for EP 11153365.9 dated Jan. 20, 2012.
Epstein, J., "Clomiphene Treatment in Oligospermic Infertile Males," Fertility and Sterility, vol. 28, No. 7, pp. 741-745 (Jul. 31, 1977).
Ernst, S., et al., "Stereochemistry of Geometric Isomers of Clomiphene: A Correction of the Literature and a Reexamination of Structure-Activity Relationships," J. Pharmaceut. Sci., vol. 65, No. 1, pp. 148-150 (Jan. 1, 1976).
Excerpt on www.medscape.com from Drug Ther. Perspect., "Toremifene: Antiestorgen for Postmenopausal Breast Cancer," vol. 10, pp. 1-5 (1997).
Feldman, H., et al., "Age Trends in the Level of Serum Testosterone and Other Hormones in Middle-Aged Men: Longitudinal Results from the Massachusetts Male Aging Study," J Clin Endocrinol Metab. 87(2), pp. 589-598 (Feb. 2002).
Anonymous: Ferring Arzneimittel: "Clomifen Ferring 50 mg Tabletten," (http://www.fachinfo.de/data/fi/jsearch?wirkstoff retrieved on May 31, 2011) pp. 1-5 (XP007918978).
Fitzpatrick, S., et al., "Effect of Estrogen Agonists and Antagonists on Induction of Progesterone Receptor in a Rat Hypothalamic Cell Line," Endocrinology, vol. 140, No. 9, pp. 3928-3937 (Sep. 1999).
Fuse, H., et al., "Changes in Seminal Plasma Transferring Concentration Following Administration of Clomiphene Citrate," Archives of Andrology, vol. 31, pp. 139-145 (Jan. 1, 1993).
Ganchev, B., et al., "Quantification of Clomiphene Metabolite Isomers in Human Plasma by Rapid-Resolution Liquid Chromatography-Electrospray Ionization-Tandem Mass Spectrometry," Anal. Bioannal. Chem., vol. 400, pp. 3429-3441 (May 1, 2011).
Garg, A., "Medical progress: Acquired and Inherited Lipodystrophies," New England Journal of Medicine, vol. 35, No. 12, pp. 1231-1232 (Mar. 18, 2004).
Glasier, A., et al., "A Comparison of the Effects on Follicular Development Between Clomiphene Citrate its Two Separate Isomers and Spontaneous Cycles," Human Reproduction, vol. 4, No. 3, pp. 252-256 (Apr. 1989).
Grinenko, G., et al., Khimiko-farmatsevticheskii Zhurnal, vol. 23, No. 1, pp. 118-123 (Jan. 1989).
Guay A., et al., "Results of Double Blinded Treatment With Clomiphene Citrate in Patients With Hypogoadotropic Hypogonadism," Annual Meeting of the Endocrine Society, Abstract No. 386, (Jun. 1993).
Guay, A., et al., "Effect of Raising Endogenous Testosterone Levels in Impotent Men with Secondary Hypogonadism: Double Blind Placebo-Controlled Trial with Clomiphene Citrate," Journal of Clinical Endocrinology and Metabolism, vol. 80, No. 12, pp. 3546-3552 (May 4, 1995).
Guay, A., et al., "Possible Hypothalamic Impotence," Urology, vol. 38, No. 4, pp. 317-322 (Oct. 1991).
Guay, A., et al., "Clomiphene Increases Free Testosterone Levels in Men with Both Secondary Hypogonadism and Erectile Dysfunction: Who Does and Does Not Benefit?" Internatl. J. Ompot. Res., vol. 15, No. 3, pp. 156-165 (Jun. 2003).
Guzick, D., et al., "Sperm Morphology, Motility and Concentration in Fertile and Infertile Men," N. Engl. J. Med., vol. 345, pp. 1388-1393 (Nov. 8, 2001).

(56) References Cited

OTHER PUBLICATIONS

Hanus, M., et al., "Antiestrogens (Tamoxifen) in the Alternative Therapy of Benign Prostatic Hyperplasial," US National Library of Medicine, Bethesda, MD, Database Medline, vol. 72, No. 7, pp. 316-318 (Oct. 1993).
Haskell, S., "Selective Estrogen Receptor Modulators," Southern Medical Journal, vol. 96, No. 5, pp. 469-476 (May 2003).
Hayashi, Norio, et al., Hinyokika Kiyo (Acta Urologica Japonica), vol. 34, No. 5, pp. 847-850 (1988) with English translation.
Healthline, Hypogonadotropic Hypogonadism, reviewed by Robert Cooper, MD, accessed Oct. 15, 2010 pp. 1-2.
Heidegger, et al., "Targeting the Insulin Like Growth Factor Network in Cancer Therapy," Cancer Biology & Therapy, vol. 11, No. 8, pp. 701-707 (Apr. 2011).
Herzog, A. G., "Reproductive Endocrine Considerations and Hormonal Therapy for Men with Epilepsy," Epilepsia, Raven Press Ltd., New York, US, vol. 32, No. Suppl. 6, pp. S34-S37, (Dec. 1, 1991).
Hirshkowitz, M., et al., "Androgen and Sleep-Related Erections," J. Psychosomatic Research, vol. 42, No. 6, pp. 541-546 (Jun. 30, 1997).
Homonnai, Z., et al., "Clomiphene Citrate Treatment in Oligozoospermia: Comparison Between Two Regimens of Low-Dose Treatment," Fertility and Sterility., vol. 60, No. 5, pp. 801-804 (Nov. 30, 1988).
International Preliminary Report on Patentability of PCT/US2009/063621 dated May 19, 2011.
International Preliminary Examination Report of PCT/US2002/21524 dated Mar. 3, 2006.
International Preliminary Report on Patentability of PCT/US2005/02500 dated Jan. 16, 2007.
International Preliminary Report on Patentability of PCT/US2006/003882 dated Aug. 7, 2007.
International Preliminary Report on Patentability of PCT/US2006/030053 dated Feb. 5, 2008.
International Preliminary Report on Patentability of PCT/US2006/10022 dated Sep. 25, 2007.
International Preliminary Report on Patentability of PCTUS2013/066141 dated May 5, 2015.
International Preliminary Report on Patentability of PCT/US2014/040704 dated Dec. 8, 2015.
International Search Report and Written Opinion of PCT/US2015/67036 dated Mar. 11, 2016.
International Search Report and Written Opinion of PCT/US2014/040704 dated Oct. 15, 2014.
International Search Report and Written Opinion of PCT/US2013/028356 dated Apr. 16, 2013.
International Search Report of PCT/US2013/032659 dated Jul. 19, 2013.
Intenrational Search Report and Written Opinion of PCTUS2013/026178 dated Jul. 22, 2013.
International Search Report of PCT/US2002/21524 dated Jun. 18, 2003.
International Search Report of PCT/US2005/02500 dated Nov. 24, 2005.
International Search Report of PCT/US2006/003882 dated Aug. 14, 2006.
International Search Report of PCT/US2006/10022 dated Jan. 10, 2007.
International Search Report of PCT/US2006/30053 dated Dec. 22, 2006.
International Search Report of PCT/US2008/075433 dated Dec. 19, 2008.
International Search Report of PCT/US2009/063621 dated Dec. 28, 2009.
International Search Report and Written Opinion of PCT/US2012/049451 dated Oct. 11, 2012.
International Search Report and Written Opinion of PCT/US2015/019493 dated Jun. 3, 2015.
International Search Report and Written Opinion of PCT/US2015/63248 dated Feb. 8, 2016.
Jarow, J., "Nonsurgical Treatment of Male Infertility: Empiric Therapy," Therapy, Chapter 23, pp. 410-422 (1991).
Jiann, B., et al., "Effect of Clomiphene on $Ca^{2+}$ Movement in Human Prostate Cancer Cells," Life Sciences, vol. 70, No. 26, pp. 3167-3178 (May 2002).
Jimenez, M., et al., "Clomiphene Prevents Cancellous Bone Loss from Tibia of Ovariectomized Rats," vol. 138, No. 5, pp. 1794-1800 (May 1, 1997).
Johansen, L. M., et al., "FDA-Approved Selective Estrogen Receptor Modulators Inhibit Ebola Virus Infection," Sci. Tansl. Med., vol. 5, pp. 190ra79-190ra79 (Jun. 19, 2013).
Jones, T. Hugh., "Testosterone Associations with Erectile Dysfunction, Diabetes, and the Metabolic Syndrome," European Urology Supplements, vol. 6, pp. 847-857 (Oct. 31, 2007).
Kaaks, R., "Nutrition, Insulin, IGF-1 Metabolism and Cancer Risk: A Summary of Epidemiological Evidence," Biology of IGF-1; Its Interaction with insulin in Health and Malignant States, vol. 262, Wiley, Chichester Novartis Foundation Symposium 262), pp. 247-260 (Jun. 10, 2005).
Kadioglu, et al., Treatment of Idiopathic and Postvaricocelectomy Oligozoospermia with Oral Tamoxifen Citrate, BJU Int., vol. 83, No. 6, pp. 646-648 (Apr. 1, 1999).
Karrer, P., "Monovalent Hydroxyl Function," Organic Chemistry, 3rd Edition, Elsevier Publishing Co., pp. 94-105 (1947).
Ke, H. Zhu, et al., "Lasofoxifene (CP-336,156), A Selective Estrogen Receptor Modulator, Prevents Bone Loss Induced by Aging and Orchidectomy in the Adult Rat," Endocrinology, vol. 141, No. 4, pp. 1338-1344 (2000) XP001170303.
Kharenko, A., et al., "Controlled Release From Oral Formulations Based on Interpolymeric Polymethacrylic Acid—Polyethylene Glycol Complex," Proceed. Intern. Symp. Control Rel. Bioact. Mater., vol. 22, pp. 232-233 (1995).
Kidd, S., et al., "Effects of male age on semen quality and fertility: A review of the literature," Fertility and Sterility, vol. 75, pp. 237-248 (Feb. 28, 2001).
Kotoulas, I., et al., "Tamoxifen Treatment in Male Infertility. I. Effect on spermatozoa," Fertil. Steril., vol. 61, No. 5, pp. 911-914 (May 31, 1994).
Laghi, F., et al., "Respiratory and Skeletal Muscles in Hypogonadal Men with Chronic Obstructive Pulmonary Disease," American Journal of Respiratory and Critical Care Medicine, vol. 171, pp. 598-605 (Mar. 15, 2005).
Lewis, B., et al., "Medical Implication of the Biological Clock," JAMA, vol. 296, pp. 2369-2371 (Nov. 15, 2006).
Lim, V., et al., "Restoration of Plasma Testosterone Levels in Uremic Men with Clomiphene Citrate," Journal of Clinical Endocrinology and Metabolism, New York, US vol. 43, No. 6, pp. 1370-1377 (Dec. 1976) XP 009041861.
Lonning, P., "Comparing cost/utility of giving an aromatase inhibitor as monotherapy for 5 years versus sequential administration following 2-3 or 5 years of tamoxifen as adjuvant treatment for postmenopausal breast cancer," Annals of Oncology, vol. 17, pp. 217-225 (Feb. 2006).
Lund, et al., "Testosterone and Andropause: The Feasibility of Testosterone Replacement Therapy in Elderly Men," Pharmacotherapy, vol. 19, No. 8, pp. 951-956 (Aug. 1, 1999).
Macrochem Press Release (Opeterone Topical Testosterone Cream, (May 12, 2010) accessed online Sep. 20, 2010.
Macleod, J., et al., "The Male Factor in Fertility and Infertility II Spermatozoon Counts in 1000 Men of Known Fertility and in 1000 Cases of Infertile Marriage," J. Urology, vol. 66, pp. 436-449 (Sep. 1951).
Makhsida, N., et al., "Hypogonadism and Metabolic Syndrome: Implications for Testosterone Therapy," J. Urology, vol. 174, pp. 827-834 (Sep. 30, 2005).
Matsumoto, A., et al., "Human Chorionic Gonadotropin and Testicular Function: Stimulation of Testosterone, Testosterone Precursors, and Sperm Production Despite High Estradiol Levels," Journal of Clinical Endocrinol. and Metab., vol. 56, No. 4, pp. 720-728 (Apr. 1983).

(56) References Cited

OTHER PUBLICATIONS

McKinlay, J., et al., "The Questionable Physiologic and Epidemiologic Basis for a Male Climacteric Syndrome: Preliminary Results from the Massachusetts Male Aging Study," Maturitas, vol. 11, No. 2, pp. 103-115 (Jun. 30, 1989).
Mazzarino, M., et al., "A Mass Spectrometric Approach for the Study of the Metabolism of Clomiphene, Tamoxifen and Toremifene by Liquid Chromatography Time-of-flight Spectroscopy," European Journal of Mass Spectrometry, vol. 14, No. 3, pp. 171-180 (Aug. 1, 2008).
Medical Information of Henan Province, "Report on 42 Cases of Treating Male Sterility with Clomiphene," vol. 2, No. 2 (Feb. 2001) (Translation).
Merck Index, 13th Ed., Entry 2410, p. 417 (2001).
Meshali, M., et al., "Effect of Interpolymer Complex Formation of Chitosan With Pectin or Acaxia on the Release Behaviour of Chlorpromazine HCl" Int. J. Phar., vol. 89, pp. 177-181 (Feb. 5, 1993).
Meso-RX, Clomid & Arimidex for Secondary Hypogonadism, Discussion in Men's Health Forum started by rbauer (Apr. 18, 2007).
Mikkelson, T., et al., "Single-Dose Pharmacokinetics of Clomiphene Citrate in Normal Volunteers," Fertility and Sterility, vol. 46, No. 3, pp. 392-396 (Sep. 30, 1986).
Morales, A., et al., "Andropause: A Misnomer for a True Clinical Entity," J. Urol., vol. 163, No. 3, pp. 705-712 (Mar. 31, 2000) Abstract.
National Institute of Diabetes and Digestive and Kidney Diseases (NIDDK) website (accessed online at http://diabetes.niddk.nih.gov on Oct. 14, 2014).
Nicholson, T., et al., "MP48095," Combination Therapy with an Aromatase Inhibitor is Needed in One Out of Six Hypogonadal Men Treated with Clomiphene Citrate, The Journal of Urology, vol. 191, No. 4S, Supplement (May 19, 2014) Abstract.
Parini, P., et al., "Importance of Estrogen Receptors in Hepatic LDL Receptor Regulation," Ateriosclerosis, Thrombosis, and Vascular Biology, vol. 17, pp. 1800-1805 (Sep. 1, 1997).
PCT Written Opinion of PCT/US02/21524 dated Nov. 25, 2005.
PCT Written Opinion of PCT/US05/02500 dated Sep. 14, 2006.
PCT Written Opinion of PCT/US06/003882 dated Aug. 4, 2007.
PCT Written Opinion of PCT/US06/10022 dated Jan. 10, 2007.
PCT Written Opinion of PCT/US06/30053 dated Dec. 22, 2006.
PCT Written Opinion of PCT/US08/075433 dated Dec. 19, 2008.
PCT Written Opinion of PCT/US09/063621 dated Dec. 28, 2009.
Petak, S., et al., American Association of Clinical Endocrinologists Medical Guidelines for Clinical Practice for the Evaluation and Treatment of Hypogonadism in Adult Male Patients, Endocrine Practice, vol. 8, pp. 440-456 (Nov./Dec. 2002).
Purvis, K., et al., "Stability of Sperm Characteristics in Men with Disturbances in Sperm Quality," Int. Journal Androl., 12, pp. 171-178 (Jun. 1989).
Rao, et al., Synthesis of Carbon-14 Labeled Clomiphene. Journal of Labelled Compounds and Radiopharmaceuticals, vol. 22, No. 3, pp. 245-255 (Mar. 1, 1985) Abstract.
Ronnberg, L., "The Effect of Clomiphene Treatment on Different Sperm Parameters in Men with Idiopathic Oligozoospermia," Andrologia, vol. 12, No. 3, pp. 261-265 (Dec. 1979).
Ross., J.W., et al., "Effect of Clomiphene Citrate and Its Isomers on Sexual Behavior in Ovariectomized Rats," Endocrinology, vol. 92, No. 4, pp. 1079-1083 (Apr. 1973) (Abstract).
Ruenitz, P., C., "Rabbit Liver Microsomal Metabolism of Enclomiphene," Drug Metabolism and Disposition, vol. 9, No. 5, pp. 456-460 (Sep. 1, 1981).
Ruenitz, et al., Cancer Research, vol. 47, pp. 4015-4109 (Aug. 1, 1987).
Ruenitz, Peter, et al., "Phenolic Metabolites of Clomiphene: [(E,Z)-2-[4-(1,2-Diphenyl-2-chlorovinyl)phenoxy]ethyl]diethylamine. Preparation, Electrophilicity, and Effects in MCF 7 Breast Cancer Cells," J. Med. Chem., vol. 32, pp. 192-197 (Jan. 1989).
Sankaran M.S., et al., "Effects of Progesterone, Oestradiol and/or Clomiphene on Liver Glycogen and Blood Glucose in Intact and Adrenalectomised Rats During Delayed Implantation," acta Endocrinologica, vol. 76, pp. 678-688 (Aug. 1, 1974).
Schultheiss, D., et al., "Testosterone Therapy in the Ageing Male: What About the Prostate?" Andrologia, vol. 36, No. 6, pp. 357-365 (May 4, 2004).
Schweikert, H., et al., "Effects of Estrogen Deprivation on Human Benign Prostatic Hyperplasia," Steroid Biochem Mol Biol., vol. 44, No. 4-6, pp. 573-576 (Mar. 31, 1993).
Shanis, B., et al., Adverse Effect of Clomiphene Citrate on Sperm Morphology, Arch. Androl., vol. 21, pp. 109 (Jan. 1, 1991).
Shida, K., et al., "Medical Treatment of Neoplasm with Steroids and Antisteroids," Chemical Abstracts Service, XP-002352053, May 12, 1984.
Shirai, Takashi, et al., Saishin-Igaku (Latest Medical Science), vol. 45, No. 11, pp. 2250-2254 (1990) with English translation.
Singh, S., et al., "Changes in Fructose & Citric Acid in Accessory Glands of Reproduction of Rats Following Long-Term Treatment With Isomers of Clomiphene Citrate," Indian Journal of Experimental Biology, vol. 11, pp. 23-26 (Jan. 1973).
Soderguard, R., et al., "Calculation of Free and Bound Fractions of Testosterone and Estradiol-17β to Human Plasma Proteins at Body Temperature," J. Steroid Biochem, vol. 16, pp. 801-810 (Jun. 1982).
Sokol, R., et al., "A Controlled Comparison of the Efficacy of Clomiphene Citrate in Male Infertility," No. 5, Fertil and Steril, vol. 49, pp. 865-870 (May 31, 1988).
Spitz, I., "Progesterone Receptor Antagonists," Current Opinion, vol. 7, No. 10, pp. 882-890 (2006).
Stahl, F., et al., "Effects of Tamoxifen on the Levels of luteinizing Hormone (LH), Follicle Stimulating Hormone FSH), Prolactin (PRL), 17 beta-oestradiol (E2), and free dihydrotestosterone (DHT) in blood of patients with Benign Prostatic Hyperplasia," US National Library of Medicine, Bethesda, MD, US, vol. 82, No. 1, pp. 21-28 (Jul. 1983).
Stedman's Medical Dictionary, William and Wilking, pp. 1312, 1439 & 1798-1799 (1995).
Steiner, M., S., et al., "Antiestrogens and Selective Estrogen Receptor Modulators Reduce Prostte Cancer Risk," World J Urol., vol. 21, pp. 31-36 (Feb. 14, 2003).
Sternbach, et al., "Age-associated Testosterone Decline in Men: Clinical Issues for Psychiatry," Am. J. Psychiatry, vol. 155, No. 10, pp. 1310-1318 (1998) Abstract.
Sterochemistry of Geometric Isomers of Clomiphene: A Correction of the Literature and a Reexamination of Structure-Activity Relationships, Journal of Pharmaceutical Science, vol. 65, No., pp. 184-150 (176) XP009056304.
Suzuki, et al., "Endocrine Environment of Benign Prostatic Hyperplasia: Prostate Size and Volume are Correlated with Serum Estrogen Concentration," Scand. J. Urol. Nephrol., vol. 29, No. 1, pp. 65-68 (1995) Abstract.
Takihara, Hiroshi, Jin to Toseki (Kidney and Dialysis) vol. 41, Special Edition, pp. 759-761 (1996) with English translation.
Tan, R.S., et al., "An Unusual Case of Vascular Hypogonadism Treated with Clomiphene Citrate and Testosterone Replacement," Andrologia, vol. 41, No. 1, pp. 63-65 (Feb. 1, 2009).
Teodosio Da Ros, C., et al., "Twenty-Five Milligrams of Clomiphene Citrate Presents Positive Effect on Treatment of Male Testosterone Deficiency—a Prospective Study," Int. Braz J. Urol., vol. 38, No. 4, pp. 512-518 (Jul.-Aug. 2012).
Tenover, J., et al., "Effects of testosterone supplementation in the aging male." J Clin. Endocrine. Metabol., vol. 75, No. 4, pp. 1092-1098 (Oct. 1992).
Tenover, J., et al., "Male Hormone Replacement Therapy Including Andropause," Endocrinology and Metabolism Clinics of North America, W.B. Saunders Company, Philadelphia, US, Dec. 1998, vol. 27, No. 4, pp. 969-987 XP008019800.
Tenover, J., et al., "Serum Bioactive and Immunoreactive Follicle-Stimulating Hormone Levels and the Response to Clomiphene in Healthy Young and Elderly Men," Journal Clinical Endocrinol. and Metab., vol. 64, No. 6, pp. 1103-1108 (Jun. 1987).
Tenover, J., et al., "The Effects of Aging in Normal Men on Bioavailable Testosterone and Luteinizing Hormone Secretion:

(56) References Cited

OTHER PUBLICATIONS

Response to Clomiphene Citrate," Journal Clinical Endocrinol. Metab., vol. 65, No. 6, pp. 1118-1126 (Dec. 1987).
Turner, R., et al., "Differential Responses of Estrogen Target Tissues in Rats Including Bone to Clomiphene, Enclomiphene, and Zuclomiphene," vol. 139, No. 9, pp. 3712-3720 (Sep. 1, 1998).
U.S. Pharmacopeia, United States Phamacopeia, 26$^{th}$ Ed., pp. 484-485 (2003).
Vippagunta, et al., "Crystalline solids" Advanced Drug Delivery Reviews, vol. 48, No. 1, pp. 3-26 (May 16, 2001).
Virginia Mason Medical Center (available online at www.virginiamason.org) accessed Mar. 2, 2011.
Wang, C., et al., "Comparison of the Effectiveness of Placebo, Clomiphene Citrate, Mesterolone, Pentoxifylline, and Testosterone Rebound Therapy for the Treatment of Idiopathic Oligospermia," Fertility and Sterility, vol. 40, No. 3, pp. 358-365 (Sep. 30, 1983).
Weissenberg, R., et al., "The Effect of Clomiphene Citrate and is Zu or En isomers on the Reproductive System of the Immature Male Rate," Andrologia, vol. 24, pp. 161-165 (1992).
Wiehle, R.D., et al., "Androxal™ (oral enclomiphene citrate) Raises Free and Total Serum Testosterone in Hypogonadal Men: Comparison with Androgel 1%®" Fertility and Sterility, vol. 82, pp. 2004-2009, (Oct. 19, 2004).
Williams, D., et al., Foye's Priciples of Medicinal Chemistry 5 Edition, Part I/Principles of Drug Discovery, Lippincott Williams & Wilkins, p. 50 (2002).
Written Opinion of Singapore Patent Applc. 2007-05640-1 dated Jul. 9, 2008.
Young, R., et al., "A Short-Term Comparison of the Effects of Clomiphene Citrate and Conjugated Equine Estrogen in Menopausal/Castrate Women," Int. J. Fertil., vol. 36, No. 3, pp. 167-171 (1991).
Young, R., et al., "Qualitative Differences in Estrogenic/Antiestrogenic Effects of Clomiphene and Zuclomiphene," Int. J. Fertil., vol. 36, No. 5, pp. 291-295 (Dec. 1990).
Young S., "Serum Concentrations of Enclomiphene and Zuclomiphene Across Consecutive Cycles of Clomiphene Citrate Therapy in Anovulatory Infertile Women," Fertility and Sterility, vol. 71, No. 4, pp. 639-644 (Apr. 30, 1999).
U.S. Appl. No. 12/205,456 Restriction Requirement dated Apr. 30, 2010.
U.S. Appl. No. 12/205,456 Non-Final Office Action dated Sep. 28, 2010.
U.S. Appl. No. 12/205,456 Final Office Action dated Mar. 7, 2011.
U.S. Appl. No. 12/205,456 Non-Final Office Action dated Apr. 24, 2012.
U.S. Appl. No. 12/205,456 Notice of Allowance dated Oct. 15, 2012.
U.S. Appl. No. 12/838,036—Notice of Allowance dated Sep. 3, 2013.
U.S. Appl. No. 12/838,036 Non-Final Office Action dated Oct. 21, 2010.
U.S. Appl. No. 12/838,036 Final Office dated May 16, 2011.
U.S. Appl. No. 13/590,045 Non-Final Office Action dated Oct. 9, 2012.
U.S. Appl. No. 13/590,045 Response to Amendment under Rule 312 dated Jun. 11, 2013.
U.S. Appl. No. 13/590,045—Notice of Allowance dated Apr. 30, 2013.
U.S. Appl. No. 10/427,768 Examiner's Interview Summary Record dated Nov. 19, 2007.
U.S. Appl. No. 10/427,768 Final office action dated Apr. 6, 2006.
U.S. Appl. No. 10/427,768 Non-final office action dated May 29, 2007.
U.S. Appl. No. 10/427,768 Non-final office action dated Oct. 12, 2005.
U.S. Appl. No. 10/427,768 Notice of Allowance and Examiner's Amendment dated Dec. 27, 2007.
U.S. Appl. No. 10/427,768 Restriction Requirement dated May 23, 2005.
U.S. Appl. No. 10/483,458 Notice of Allowance dated Apr. 21, 2010.
U.S. Appl. No. 10/483,458 Final Office dated Mar. 17, 2010.
U.S. Appl. No. 10/483,458 Non-final office action dated Jul. 20, 2009.
U.S. Appl. No. 10/483,458 Advisory Action dated Jan. 16, 2009.
U.S. Appl. No. 10/483,458 Final office action dated Nov. 19, 2008.
U.S. Appl. No. 10/483,458 Non-final office action dated Feb. 13, 2008.
U.S. Appl. No. 10/483,458 Restriction Requirement dated Oct. 25, 2007.
U.S. Appl. No. 10/712,546 Non-final office action dated Mar. 15, 2006.
U.S. Appl. No. 10/712,546 Notice of Allowance dated Sep. 29, 2006.
U.S. Appl. No. 10/712,546 Restriction Requirement dated Nov. 10, 2005.
U.S. Appl. No. 11/750,190 Restriction Requirement dated Mar. 27, 2009.
U.S. Appl. No. 11/750,190 Non-final office action dated Aug. 11, 2009.
U.S. Appl. No. 11/750,190 Notice of Allowance dated Jan. 8, 2010.
U.S. Appl. No. 11/750,190 Notice of Allowance dated Feb. 5, 2010.
U.S. Appl. No. 11/571,150 Restriction Requirement dated Aug. 31, 2009.
U.S. Appl. No. 11/571,150 Non-final office action dated Oct. 14, 2009.
U.S. Appl. No. 11/997,858 Restriction Requirement dated Aug. 28, 2009.
U.S. Appl. No. 11/815,542 Restriction Requirement dated Aug. 31, 2009.
U.S. Appl. No. 11/815,542 Non-final office action dated Oct. 15, 2009.
U.S. Appl. No. 11/815,542 Final Office action dated Mar. 30, 2010.
U.S. Appl. No. 11/815,542 Advisory Action dated Jun. 16, 2010.
U.S. Appl. No. 11/815,542 Non-final office action dated May 10, 2011.
U.S. Appl. No. 11/815,542 Final Office action dated Nov. 15, 2011.
U.S. Appl. No. 11/815,542 Non-Final Office Action dated Feb. 28, 2012.
U.S. Appl. No. 11/815,542 Notice of Allowance dated Apr. 18, 2012.
U.S. Appl. No. 11/814,068 Non-final office action dated Apr. 12, 2011.
U.S. Appl. No. 13/196,688 Notice of Allowance dated Oct. 16, 2012.
U.S. Appl. No. 13/590,045 Notice of Allowance dated Apr. 30, 2013.
U.S. Appl. No. 14/378,573—Non-final office action dated Jan. 22, 2015.
U.S. Appl. No. 14/378,573—Notice of Allowance dated Jun. 10, 2015.
U.S. Appl. No. 14/886,874—Restriction Requirement dated Feb. 9, 2016.
U.S. Appl. No. 13/764,574—Non-final office action dated Oct. 23, 2014.
U.S. Appl. No. 13/764,574—Restriction Requirement dated Jun. 6, 2014.
U.S. Appl. No. 13/764,574—Final Office action dated Jun. 26, 2015.
U.S. Appl. No. 13/764,574—Non-final office action dated Dec. 17, 2015.
U.S. Appl. No. 13/764,574—Final Office Action dated Jun. 9, 2016.
U.S. Appl. No. 14/380,342—Non-final office action dated Jun. 1, 2015.
U.S. Appl. No. 14/380,342—Final office action dated Dec. 7, 2015.
U.S. Appl. No. 14/085,494—Non-final office action dated Dec. 15, 2014.
U.S. Appl. No. 14/085,494—Final Office Action dated Apr. 19, 2016.
U.S. Appl. No. 14/236,868—Restriction Requirement dated Oct. 2, 2015.

(56) References Cited

OTHER PUBLICATIONS

U.S. Appl. No. 14/236,868—Non-final office action dated Feb. 12, 2016.
U.S Appl. No. 14/421,119—Restriction Requirement dated Oct. 5, 2015.
U.S. Appl. No. 14/421,119—Non-final office action dated May 6, 2016.
U.S. Appl. No. 14/440,007—Non-final office action dated Jun. 24, 2016.
U.S. Appl. No. 14/896,043—Non-final office action dated Apr. 22, 2016.
U.S. Control No. 90/008,024 Non-final office action dated Nov. 1, 2006.
U.S. Control No. 90/008,024 Examiner Interview Summary Record dated Dec. 13, 2006.
U.S. Control No. 90/008,024 Non-final office action dated Jan. 29, 2007.
U.S. Control No. 90/008,024 Final office action dated Jun. 22, 2007.
U.S. Control No. 90/008,024 Examiner Interview Summary Record dated Jul. 25, 2007.
U.S. Control No. 90/008,024 Final office action dated Nov. 16, 2007.
U.S. Control No. 90/008,024 Advisory Action dated Feb. 1, 2008.
U.S. Control No. 90/008,024 Advisory Action dated Mar. 5, 2008.
U.S. Control No. 90/008,024 Examiner's Answer dated Jun. 12, 2008.
U.S. Control No. 90/008,024 Decision on Appeal dated Aug. 28, 2009.
U.S. Control No. 90/008,024 Decision on Request for Rehearing dated Aug. 2, 2010.
U.S. Control No. 90/006,921 Non-final office action dated Sep. 9, 2004.
U.S. Control No. 90/006,921 Examiner's Interview Summary dated Nov. 20, 2004.
U.S. Control No. 90/006,921 Final office action dated Feb. 23, 2005.
Chaumeil, J.C., Micronization: A Method of Improving the Bioavailability of Poorly Soluble Drugs, Methods Find. Exp. Clin. Pharmacol., vol. 20, No. 3, pp. 211 (Apr. 1998)—Abstract.
Hill, S., et al., "Enclomiphene, an Estrogen Receptor Antagonist for the Treatment of Testosterone Deficiency in Men," IDrugs: the Investigational Drugs Journal, vol. 12, No. 2, pp. 109-119 (Mar. 2009).
Hobbs, C.J., et al., "Testosterone Administration Increases Insulin-Like Growth Factor-I Levels in Normal Men," Journal of Clinlical Endocrinology & Metabolism, vol. 77, Issue 3, published online Jan. 14, 2009 (Abstract).
Lee, D., et al., PD45-08 "Comparison of Clomiphene Citrate and Transdermal Testosterone Replacement Therapy in Their Influence on Hormonal and Metabolic Changes in the Treatment of Hypogonadism," The Journal of Urology, vol. 193, No. 4S, Supplement, pp. e904-e905 (May 18, 2015).
Shiau, A., et al., "The Structural Basis of Estrogen Receptor/Coactivator Recognition and the Antagonism of This Interaction by Tamoxifen," Cell, vol. 95, pp. 927-937 (Dec. 23, 2998).
U.S. Appl. No. 14/380,342—Final Office Action dated Mar. 15, 2017.
U.S. Appl. No. 14/440,007—Notice of Allowance dated Feb. 16, 2017.

* cited by examiner

Normal Secretory Total Serum Testosterone Profiles in Healthy Young and Older Men

— # TRANS-CLOMIPHENE METABOLITES AND USES THEREOF

This application is the 35 U.S.C. 371 National Stage of International Application Number PCT/US2012/049451, filed Aug. 3, 2012 and claims the benefit, under 35 USC 119(e), of U.S. Provisional Patent Application No. 61/515,278, filed Aug. 4, 2011, the entire contents of which are hereby incorporated by reference.

FIELD OF THE INVENTION

The present invention relates to metabolites of trans-clomiphene in substantially pure form, pharmaceutical compositions comprising same and methods for treating various hormone-dependent disorders.

BACKGROUND

Clomiphene is a selective estrogen receptor modulator related to tamoxifen. Clomiphene binds to estrogen receptors and blocks the normal estrogen feedback on the hypothalamus and subsequent negative feedback on the pituitary. This leads to increases in luteinizing hormone (LH) and follicle stimulating hormone (FSH). In men, these increased levels of gonadotropins stimulate the Leydig cells of the testes and result in the production of higher testosterone levels. For example, Tenover et al., J. Clin. Endocrinol. Metab. 64:1103, (1987) and Tenover et al., J. Clin. Endocrinol. Metab. 64:1118 (1987) found increases in FSH, LH in both young and old men after treatment with clomiphene. They also found increases in free and total testosterone in men with young men showing significant increases.

In females, clomiphene is currently approved as a mixture of both cis- and trans-isomers, the cis-isomer being present as about 30% to 50% (Merck Manual) for the induction of ovulation in anovulatory women. The increases in LH and FSH in anovulatory females following administration of clomiphene result in follicular growth and ultimately ovulation. The drug is recommended to be administered for 5 days at a dose of up to 100 mg daily Ernst et al., J. Pharmaceut. Sci. 65:148 (1976), have shown that clomiphene is a mixture of two geometric isomers which they refer to as cis,-Z-, clomiphene (cis-clomiphene or zuclomiphene) and trans-,E-, clomiphene, (trans-clomiphene or enclomiphene). According to Ernst, et al. trans-clomiphene HCl has a melting point of 149° C.-150.5° C., while cis-clomiphene HO has a melting point of 156.5° C.-158° C. Ernst et al. have also noted that (the trans-isomer) is antiestrogenic (AE) while the cis-isomer is the more potent and more estrogenic form and has also been reported to have anti-estrogenic activity. The authors attribute the effect of the drug on ovulatory activity to both forms stating that the mixture is more effective than trans-clomiphene alone. The trans-isomer aids ovulation at the level of the hypothalamus. The estrogenic isomer cis-clomiphene contributes to enhanced ovulation elsewhere in the physiologic pathway leading to ovulation. The isomers are also reported to have different in vivo half-life. The cis isomer has been reported to leave residual blood levels for in excess of one month following a single dose.

Clomiphene has been associated with numerous side effects including: blurred vision, abdominal discomfort, gynecomastia, testicular tumors, vasomotor flushes, nausea, and headaches. Furthermore, other studies suggest that clomiphene possesses both genotoxic and tumor enhancement effects. The net outcome of these observations is that clomiphene in its current format, having between 30% and 50% of the cis isomer, would be unacceptable for chronic therapy in men for the treatment of testosterone deficiency.

Oral administration of trans-isomer of clomiphene (trans-clomiphene or enclomiphene) has been demonstrated to be effective in the treatment of a panoply of disorders ranging from secondary hypogonadism in males to induction of ovulation in anovulatory females. However, first pass metabolism of the drug by the liver requires relatively high doses to be administered orally to achieve therapeutic effect. A significant advance in the art would result if active metabolites of trans-clomiphene were discovered.

SUMMARY

The present invention provides substantially pure metabolites of trans-clomiphene and salts thereof, preferably the citrate salt. Pharmaceutical compositions comprising a substantially pure metabolite of trans-clomiphene or a salt thereof and a pharmaceutically acceptable carrier are also provided.

The present invention is also related to methods for treating and/or preventing disorders that are ameliorated by administration of an effective amount of trans-clomiphene. In other words, the present invention provides a method for treating any disorder which may be treated with trans-clomiphene, comprising administering a therapeutically effective amount of a substantially pure trans-clomiphene metabolite or pharmaceutical composition comprising same to a patient in need of such treatment.

Examples of disorders that are ameliorated by administration of an effective amount of trans-clomiphene (and which therefore may be treated according to the present invention) include, without limitation, secondary hypogonadism, type 2 diabetes, elevated cholesterol, elevated triglycerides, wasting, lipodystrophy, female and male infertility, benign prostate hypertrophy, prostate cancer, breast cancer, uterine cancer and ovarian cancer.

DETAILED DESCRIPTION

Figure 1:
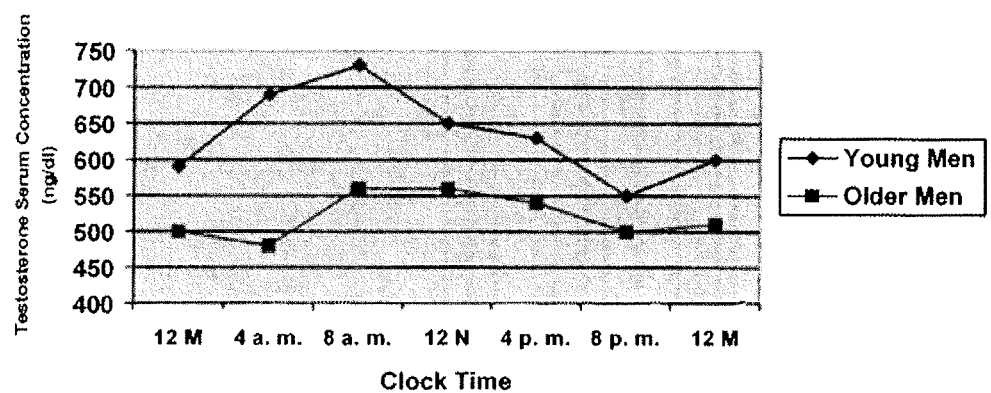
FIG. 1 is a graphic representative of the normal secretory total serum testosterone profiles in healthy men (young and old).
Figure 2:
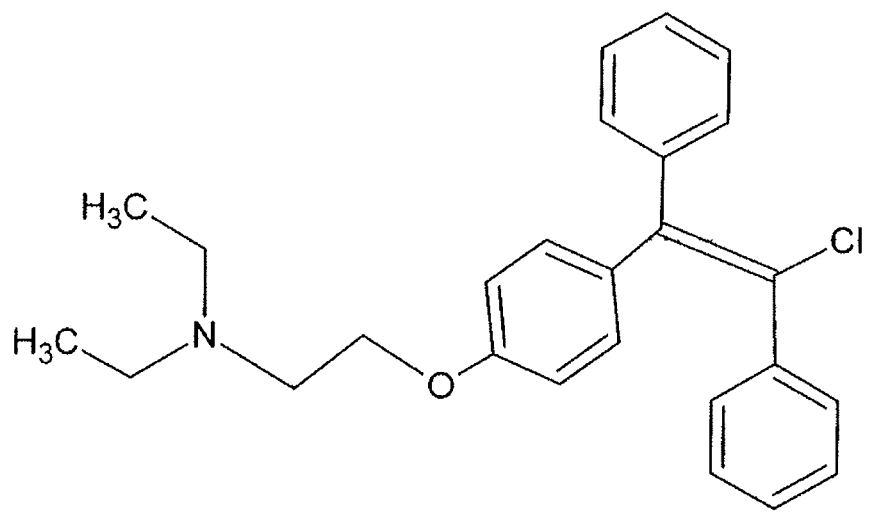
FIG. 2 shows the chemical structure of trans-clomiphene.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any way. Embodiments illustrated under any heading may be combined with embodiments illustrated under any other heading.

It is to be understood that any ranges, ratios and ranges of ratios that can be formed by any of the numbers or data present herein represent further embodiments of the present invention. This includes ranges that can be formed that do or do not include a finite upper and/or lower boundary. Accordingly, the skilled person will appreciate that many such ratios, ranges and ranges of ratios can be unambiguously derived from the data and numbers presented herein and all represent embodiments of the invention.

Before the present compounds, compositions and methods are disclosed and described, it is to be understood that the terminology used herein is for the purpose of describing particular embodiments only and is not intended to be limiting. It must be noted that, as used in the present specification and the appended claims, the singular forms "a," "an" and "the" include plural referents unless the context clearly dictates otherwise.

Definitions

The term "oral" administration means that the active agent is in a formulation designed to be ingested, i.e. designed to be delivered to the gastrointestinal system for absorption.

The term "effective dosage" means an amount of the composition's active component sufficient to treat a particular condition.

The term "treat" or "treatment" as used herein refers to any treatment of any progesterone-dependent disorder or disease, and includes, but is not limited to, inhibiting the disorder or disease arresting the development of the disorder or disease; relieving the disorder or disease, for example, causing regression of the disorder or disease; or relieving the condition caused by the disease or disorder, relieving the symptoms of the disease or disorder.

The term "prevent" or "prevention," in relation to a progesterone-dependent disorder or disease, means preventing the onset of disorder or disease development if none had occurred, or preventing further disorder or disease development if the disorder or disease was already present.

The term "substantially pure" means a compound of the present invention having purity greater than about 80%, preferably greater than about 90%, more preferably greater than 95% and most preferably having purity greater than about 99% as measured by high performance liquid chromatography (HPLC).

The term "pharmaceutically acceptable salt" refers to a salt prepared from a pharmaceutically acceptable non-toxic inorganic or organic acid. Inorganic acids include, but are not limited to, hydrochloric, hydrobromic, hydroiodic, nitric, sulfuric, and phosphoric. Organic acids include, but are not limited to, aliphatic, aromatic, carboxylic, and sulfonic organic acids including, but not limited to, formic, acetic, propionic, succinic, benzoic camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, alginic, and galacturonic acid. A preferred salt is the citrate salt.

In various embodiments, the present invention provides metabolites of trans-clomiphene in substantially pure form. The metabolites may be purified from an appropriate source or may be synthetically produced in a purified and isolated form. For example, metabolites of the invention may be identified and isolated or separated from body tissues or fluids of a test animal following administration of trans-clomiphene. Alternatively, metabolites of the invention may be identified and isolated from animal hepatocytes following incubation with trans-clomiphene.

In one aspect, the metabolite may result from the action of liver enzymes of the cytochrome P450 (CYP) family. The metabolism of oral agents is often due to the action of these enzymes which reside in liver hepatocytes. Such "first pass" metabolism, in which drugs pass from the gut through the liver before distribution to the body, represents a potential barrier to the transfer of active pharmaceutical agents from the digestive tract to the bloodstream. The CYP enzymes fall into distinct classes and have analogous members throughout the mammals.

In various embodiments, the present invention provides a trans-clomiphene metabolite produced by the catalytic action of a member of the CYP2 or CYP3 family. In preferred embodiments, the metabolite is produced primarily through catalytic action of CYP2D6 and/or CYP3A4 and/or CYP3A5.

In one embodiment, the present invention provides a trans-clomiphene metabolite having a chemical formula selected from: C26H29NO4; C27H31NO3; C26H30NO3Cl; C32H36NO8Cl; C26H30NO3Cl; C27H30NO3Cl; C32H36NO8Cl; C26H28NO3Cl; C36H43N4O7SCl; C26H30NO3Cl; C36H43N4O7SCl; C27H31NO3; C24H24NO2Cl; C26H28NO2Cl; C27H30NO3Cl; C27H30NO6ClS; C26H28NO3Cl; C26H28NO7Cl; C26H28NO2Cl; C27H30NO3Cl; C24H24NOCl; C26H28NO2Cl; and C24H24NO2Cl.

In a preferred embodiment, the trans-clomiphene metabolite has a chemical formula selected from: C26H30NO3Cl, C26H28NO2Cl, C27H30NO3Cl, and C24H24NOCl.

In a particularly preferred embodiment, the present invention provides a substantially pure trans-clomiphene metabolite, 4-hydroxy-trans-clomiphene (or 4-OH-trans-clomiphene) produced by the catalytic action of CYP2D6 having the formula

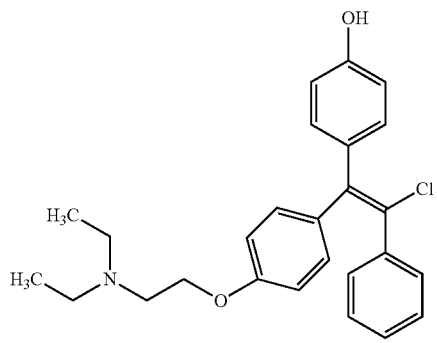 [SMILES: CCN(CC)CCOc1ccc(/C(=C(/Cl)c2ccccc2)c2ccc(O)cc2)cc1]

and pharmaceutically acceptable salts thereof. This metabolite is formed by 4-hydroxylation at the para position of the trans-clomiphene phenyl ring.

In a preferred embodiment, the present invention provides a substantially pure trans-clomiphene metabolite, 4'-hydroxy-trans-clomiphene (or 4'-OH-trans-clomiphene), produced by the catalytic action of CYP2B6 having the formula

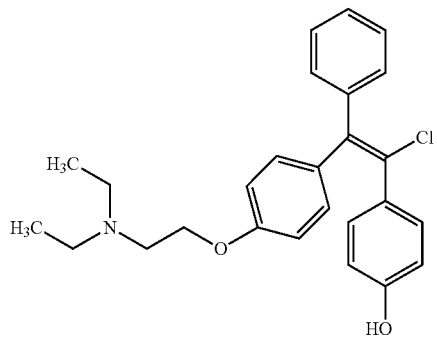 [SMILES: CCN(CC)CCOc1ccc(/C(=C(/Cl)c2ccc(O)cc2)c2ccccc2)cc1]

and pharmaceutically acceptable salts thereof. This metabolite is formed by 4'-hydroxylation at the para position of the trans-clomiphene phenyl ring.

In another preferred embodiment, the present invention provides a substantially pure trans-clomiphene metabolite, 3-hydroxy-trans-clomiphene (or 3-OH-trans-clomiphene), produced by the catalytic action of CYP3A4 or CYP3A5 having the formula

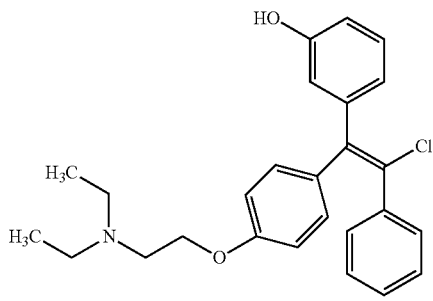 [SMILES: CCN(CC)CCOc1ccc(/C(=C(/Cl)c2ccccc2)c2cccc(O)c2)cc1]

and pharmaceutically acceptable salts thereof.

In another particularly preferred embodiment, the present invention provides a substantially pure trans-clomiphene metabolite, N-desethyl-trans-clomiphene, produced by the catalytic action of CYP3A4 or CYP3A5 having the formula

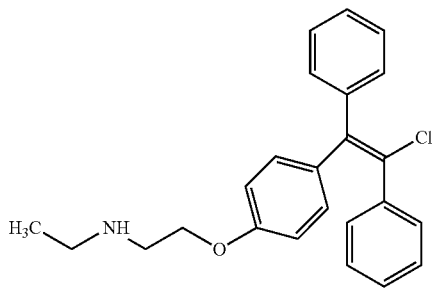 [SMILES: CCNCCOc1ccc(/C(=C(/Cl)c2ccccc2)c2ccccc2)cc1]

and pharmaceutically acceptable salts thereof. This metabolite is formed by N-desalkylation of an ethyl group from trans-clomiphene.

In another preferred embodiment, the present invention provides a substantially pure trans-clomiphene metabolite, 3,4-dihydroxy-trans-clomiphene, produced by the sequential catalytic action of CYP3A4/5 and CYP2D6 having the formula

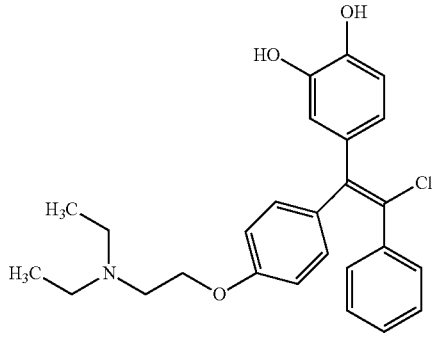 [SMILES: CCN(CC)CCOc1ccc(/C(=C(/Cl)c2ccccc2)c2ccc(O)c(O)c2)cc1]

and pharmaceutically acceptable salts thereof.

In a related preferred embodiment, the metabolite produced by the sequential action of CYP3A4/5 and CYP2D6 is further modified such that a double bound is reduced. Accordingly, the present invention also provides a substantially pure trans-clomiphene metabolite having the formula

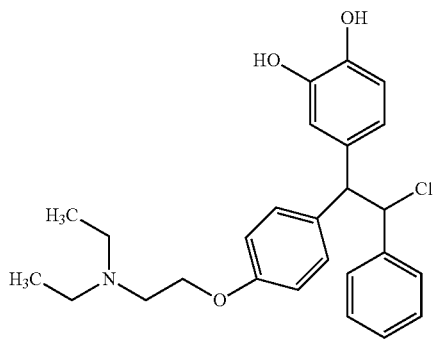 [SMILES: CCN(CC)CCOc1ccc(C(c2ccc(O)c(O)c2)C(Cl)c2ccccc2)cc1]

(C26H30NO3Cl)

In another related preferred embodiment, the metabolite produced by the sequential action of CYP3A4/5 and CYP2D6 is mono-methylated. Accordingly, the present invention also provides a substantially pure trans-clomiphene metabolite having the chemical formula C27H30NO3Cl. The mono-methylated metabolite may have any one of the following structural formulas:

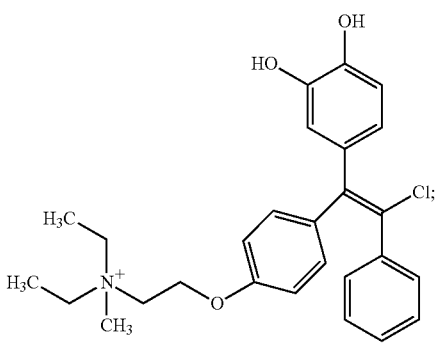

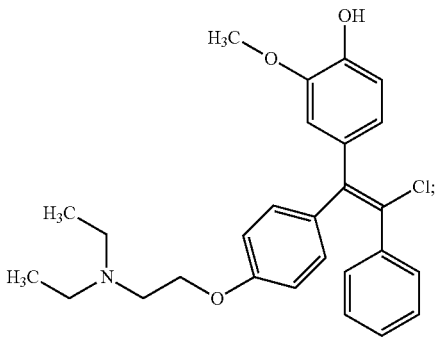

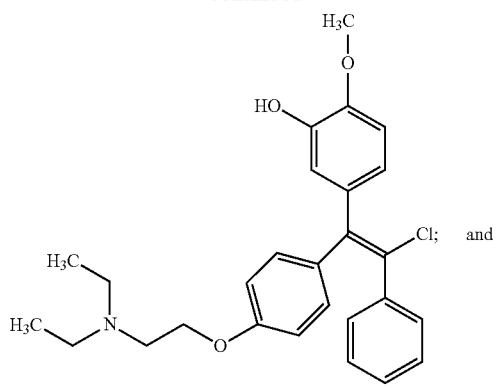

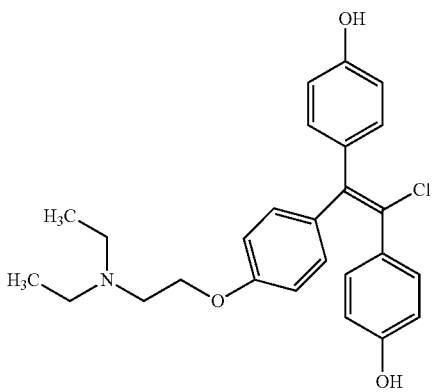

and pharmaceutically acceptable salts thereof.

In various embodiments, the present invention also provides pharmaceutical compositions comprising one or more trans-clomiphene metabolites or salts thereof as described and a pharmaceutically acceptable carrier, which can be used in the methods described herein.

In various embodiments, the present invention also provides the use of a trans-clomiphene metabolite or salt thereof (or pharmaceutical composition comprising same) in the treatment of a trans-clomiphene-responsive disorder in a patient.

In one embodiment, a method for elevating testosterone levels is provided comprising administering an effective amount of a trans-clomiphene metabolite or salt thereof (or pharmaceutical composition comprising same) to a patient in need of such treatment. In a related embodiment, a method for treating a disorder related to testosterone deficiency including, without limitation, oligospermia, azoospermia, wasting and depression is provided. The use of trans-clomiphene for elevating testosterone levels in a mammal is described in U.S. Pat. No. 7,759,360, the entire content of which is hereby incorporated by reference, in particular at column 4, line 51 to column 6, line 5. In one preferred embodiment, the trans-clomiphene metabolite is 4-OH-trans-clomiphene. In another preferred embodiment the patient is a human male with secondary hypogonadism.

In a related embodiment, a method for treating secondary hypogonadism in a human male is provided comprising administering an effective amount of a trans-clomiphene metabolite or salt thereof (or pharmaceutical composition comprising same) to a patient in need of such treatment. In a preferred embodiment, the trans-clomiphene metabolite is 4-OH-trans-clomiphene.

In another embodiment, a method for decreasing cholesterol levels is provided, comprising administering an effective amount of a trans-clomiphene metabolite or salt thereof (or pharmaceutical composition comprising same) to a patient in need of such treatment. The use of trans-clomiphene for decreasing cholesterol levels is described in U.S. Pat. No. 7,368,480, the entire content of which is hereby incorporated by reference, in particular at column 4, line 66 to column 6 line 10. In one preferred embodiment, the trans-clomiphene metabolite is 4-OH-trans-clomiphene. In another preferred embodiment the patient is a human male with secondary hypogonadism In another embodiment, a method for treating and/or preventing a condition selected from the group consisting of benign prostate hypertrophy, prostate cancer and elevated triglycerides is provided comprising administering an effective amount of a trans-clomiphene metabolite or salt thereof

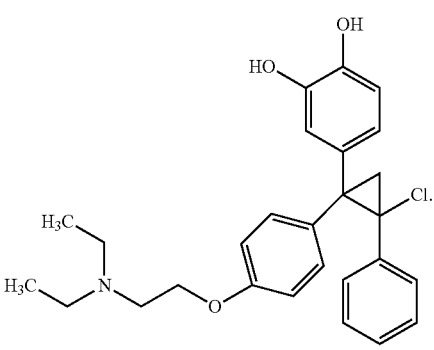

In another preferred embodiment, the present invention provides a substantially pure trans-clomiphene metabolite produced by the sequential catalytic action of CYP3A4/5 and CYP2B6 having the formula

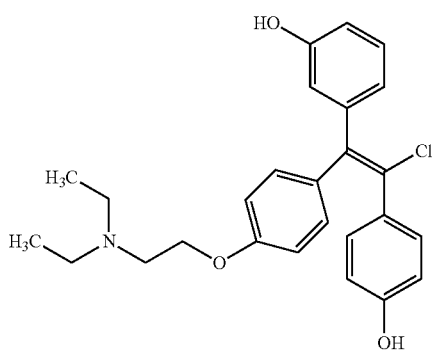 [SMILES: CCN(CC)CCOc1ccc(/C(=C(/Cl)c2ccc(O)cc2)c2cccc(O)c2)cc1]

and pharmaceutically acceptable salts thereof.

In another preferred embodiment, the present invention provides a substantially pure trans-clomiphene metabolite produced by the sequential catalytic action of CYP2D6 and CYP2B6 having the formula (or pharmaceutical composition comprising same) to a patient in need of such treatment. The use of trans-clomiphene for treating benign prostate hypertrophy, prostate cancer and elevated triglycerides is described in US Patent Application Publication No. 2008/0242726, the entire content of which is hereby incorporated by reference, in particular at page 3, paragraph [0030] to page 4, paragraph [0041]. In one preferred embodiment, the trans-clomiphene metabolite is 4-OH-trans-clomiphene. In another preferred embodiment the patient is a human male with secondary hypogonadism.

In another embodiment, a method for treating infertility in a human male is provided comprising administering an effective amount of a trans-clomiphene metabolite or salt thereof (or pharmaceutical composition comprising same) to a human male in need of such treatment. The use of trans-clomiphene for treating male infertility is described in US Patent Application Publication No. 2009/0215906, the entire content of which is hereby incorporated by reference, in particular at page 2, paragraph [0029] to page 3, paragraph [0034]. In one preferred embodiment, the trans-clomiphene metabolite is 4-OH-trans-clomiphene. In another preferred embodiment the patient is a human male with secondary hypogonadism.

In another embodiment, a method for preventing the transition from metabolic syndrome to type 2 diabetes is provided comprising administering an effective amount of a trans-clomiphene metabolite or salt thereof (or pharmaceutical composition comprising same) to a human male with secondary hypogonadism. The use of trans-clomiphene for preventing the transition from metabolic syndrome to type 2 diabetes mellitus in such a patient population is described in US Patent Application Publication No. 2009/0099265, the entire content of which is hereby incorporated by reference, in particular at page 3, paragraph [0040]. In a preferred embodiment, the trans-clomiphene metabolite is 4-OH-trans-clomiphene.

In yet another embodiment, a method for reducing fasting blood glucose levels is provided comprising administering an effective amount of a trans-clomiphene metabolite or salt thereof (or pharmaceutical composition comprising same) to a human male with secondary hypogonadism. The use of trans-clomiphene for reducing fasting blood glucose levels in such a patient population is described at paragraph [0041] of US Patent Application Publication No. 2009/0099265. In a preferred embodiment, the trans-clomiphene metabolite is 4-OH-trans-clomiphene.

In yet another embodiment, a method for treating type 2 diabetes mellitus is provided comprising administering an effective amount of a trans-clomiphene metabolite or salt thereof (or pharmaceutical composition comprising same) to a human male with secondary hypogonadism. The use of trans-clomiphene for treating type 2 diabetes mellitus in such a patient population is described at paragraph [0042] of US Patent Application Publication No. 2009/0099265. In a preferred embodiment, the trans-clomiphene metabolite is 4-OH-trans-clomiphene.

In another embodiment, a method for the treatment of female infertility is provided comprising administering an effective amount of a trans-clomiphene metabolite or salt thereof (or pharmaceutical composition comprising same) to a female in need of such treatment. Preferably the trans-clomiphene metabolite is administered as a daily dose in the early follicular phase of the menstrual cycle for five consecutive days. For example, an administration schedule could involve administration on days 5 to 9 or on days 3 to 7 of the menstrual cycle. Preferably the patient is an anovulatory female.

In another embodiment, a method for the treatment and/or prevention of breast cancer is provided comprising administering an effective amount of a trans-clomiphene metabolite or salt thereof (or pharmaceutical composition comprising same) to a female in need of such treatment. According to this embodiment, the trans-clomiphene metabolite may be administered to a female at increased risk for developing breast cancer in order to prevent the development of breast cancer. Alternatively, the trans-clomiphene metabolite may be administered to a female with breast cancer in order to treat the breast cancer. The trans-clomiphene metabolite may also be administered as an adjuvant therapy following initial treatment with surgery in order to minimize the possibility of relapse. Preferably when administered as an adjuvant, the trans-clomiphene is administered for a period of about 5 years.

In another embodiment, a method for the treatment of endometrial (or uterine) cancer is provided comprising administering an effective amount of a trans-clomiphene metabolite or salt thereof (or pharmaceutical composition comprising same) to a female in need of such treatment.

In yet another embodiment, a method for the treatment of ovarian cancer is provided comprising administering an effective amount of a trans-clomiphene metabolite or salt thereof (or pharmaceutical composition comprising same) to a female in need of such treatment.

In various embodiments, the invention provides intermittent dosing procedures useful in the treatment methods described herein.

By "intermittent administration" it is meant a period of administration of a therapeutically effective dose of a trans-clomiphene metabolite, followed by a time period of discontinuance, which is then followed by another period of administration of a therapeutically effective dose, and so forth.

The administration period of the therapeutically effective dose may comprise continuous dosing, as for example with a sustained-release formulation, or may comprise daily, weekly, monthly, or therebetween, dosing, as for example, with one, two or more tablets per day, so long as the dosing interval during the administration period is less than the discontinuance period.

The preferred length of the discontinuance period depends on the concentration and frequency of administration of the effective dose during the administration period and in any case should be chosen such that the desired therapeutic effect is achieved during the treatment period. For example, where the trans-clomiphene metabolite or salt thereof (or pharmaceutical composition comprising same) is administered to elevate testosterone levels, the discontinuance period should be terminated before testosterone levels fall below about 300 ng/DL.

Pharmaceutical compositions according to the present invention may comprise or consist essentially of a trans-clomiphene metabolite of the invention at a dosage between about one mg to about 200 mg (although the determination of optimal dosages is with the level of ordinary skill in the art). The composition may comprise a trans-clomiphene metabolite of the invention at a dosage of about 1 mg, 2 mg, 3, mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg or there between.

Pharmaceutical compositions may comprise 100% w/w of a trans-clomiphene metabolite or may additionally comprise other active agents useful in achieving the desired therapeutic effect. Where the pharmaceutical composition comprises 100% w/w of a trans-clomiphene metabolite, one or more additional active agents may be separately co-administered sequentially or simultaneously to achieve a desired therapeutic effect.

Dosages are preferably (but not necessarily) administered as part of a dosage regimen designed to give rise to serum testosterone levels that mimic or correspond to the normal secretary total serum testosterone profile described in FIG. 1 during the period of administration and preferably during the period of discontinuance as well. For example, according to FIG. 1 a dosage of the preferred composition may be administered in a pharmaceutical formulation that would give rise to peak serum testosterone levels at around 8 a.m. Such pharmaceutical formulations may be in the form of sustained release formulations prepared as described for example in U.S. Pat. No. 6,221,399, Japanese patent 4-312522, Meshali et al, Int. J. Phar. 89:177-181 (1993), Kharenko et al, Intern. Symp. Control Rel. Bioact. Mater. 22:232-233 (1995), WO 95/35093, Dangprasit et al., Drug. Devel. and Incl. Pharm. 21 (20):2323-2337 (1995); U.S. Pat. Nos. 6,143,353, 6,190,591, 6,096,338, 6,129,933, 6,126,969, 6,248,363 and other sustained release formulations well known in the art.

The terms "treat" or "treatment" as used in the instant application, refer to both therapeutic treatment and prophylactic or preventative measures, wherein the object is to prevent or slow down (lessen) an undesired physiological or psychological change or disorder, such as symptoms associated with secondary hypogonadism. For purposes of the present invention, beneficial or desired clinical results include, but are not limited to, alleviation of symptoms, diminishment of extent of disease, stabilized (i.e., not worsening) state of disease, delay or slowing of disease progression, amelioration or palliation of the disease state and remission (whether partial or total), whether detectable or undetectable. "Treatment" can also mean prolonging survival as compared to expected survival if not receiving treatment. Individuals in need of treatment include those already with the condition or disorder as well as those prone to develop the condition or disorder or those in whom the condition or disorder is to be prevented.

Suitable pharmaceutical compositions or unit dosage forms may be in the form of solids, such as tablets or filled capsules or liquids such as solutions, suspensions, emulsions, elixirs or capsules filled with the same, all for oral use. The compositions may also be in the form of sterile injectable solutions or emulsions for parenteral (including subcutaneous) use. The compositions may also be formulated for topical administration. For example, the composition may be formulated as a lotion, cream, ointment, gel, foam, or transdermal patch. In one preferred embodiment, the composition is formulated as a gel (e.g. an aqueous alcoholic gel) for transdermal administration (e.g. to the scrotum). Such pharmaceutical compositions and unit dosage forms thereof may comprise ingredients in conventional proportions.

Although oral administration is the preferred route, compositions according to the present invention may be administered by any route of administration including, but not limited to, intravenous, subcutaneous, buccal, transmucosal, intrathecal, intradermal, intracisternal, intramuscular, transdermal, intraperitoneal, epidural, vaginal, rectal, intranasal, sublingual, intra-articular, intra-cerebrospinal and intrasynovial. After administration of the composition, serum testosterone levels may be measured as described above and dosages may be altered to achieve a sufficient increase in the serum testosterone levels to achieve the desired physiological results associated with normal testosterone described above.

Compositions of the present invention may also be administered in fast-release formulations, slow-release formulations or mixtures of fast-release and slow-release formulations such as a multi-layer tablet comprising at least one fast-release layer and at least one slow-release layer.

All of the references discussed herein are incorporated by reference in their entirety.

The following Examples are meant to be illustrative of the invention and are not intended to limit the scope of the invention as set out is the appended claims.

EXAMPLE 1

In Vitro Metabolite Profile of Androxal® (Trans-Clomiphene)

A study was conducted to determine the metabolic profile of Androxal® in cryopreserved hepatocytes from Sprague-Dawley rat, Beagle dog, cynomolgus monkey, and human. The liver is the main site of drug metabolism and the full complement of hepatic drug metabolizing enzymes (including liver enzymes of the CYP P450 family) are maintained within the intact cell. Isolated liver hepatocytes constitute a physiologically relevant experimental model for the evaluation of liver-related drug properties such as metabolism. Cyropreservation of the hepatocytes greatly enhances their availability for studies.

Primary hepatocytes isolated from several donors for each animal species and five human donors were pooled according to species and cryopreserved. The hepatocytes were thawed, subjected to Percoll density gradient centrifugation to remove debris and counted to determine yield. Viability was measured using Trypan blue exclusion. The hepatocytes were diluted with CYP assay buffer (Krebs-Hensleit Buffer) to prepare a 2× cell suspension of $2.0 \times 10^6$ viable cells/ml. Aliquots of the 2× hepatocyte suspension (0.5 ml containing $1.0 \times 10^6$ cells) were transferred to appropriate wells for a final 1× cell density of $1.0 \times 10^6$ cells/well. All incubations were conducted at $37 \pm 1°$ C., 95% air/5% $CO_2$, and saturating humidity in 12-well uncoated culture plates. Aliquots of 2× Androxal® dosing solutions (0.5 ml containing 6 and 60 μM Androxal®) were added to each appropriate well for a total final volume of 1 ml. The cultures were incubated for 1 and 4 hours. The sample size was N=2 replicates.

Matrix control samples were included as a source of background matrix components to aid in metabolite identification. Equal volumes of 2× hepatocyte suspension and CYP assay buffer without Androxal® were combined and incubated for 4 hours.

Chemical degradation control samples were included to evaluate the possibility of chemical degradation of Androxal® in the absence of cells. Equal volumes of 2× Androxal® dosing solution (6 and 60 μM) and CYP buffer were combined and incubated for 1 and 4 hours.

Metabolic positive control samples were included to evaluate the metabolic capacity of the cryopreserved hepatocytes from each species. Equal volumes of 2×7-Ethoxycoumarin dosing solutions (150 μM) and 2× hepatocyte suspension were combined and incubated for 1 and 4 hours.

The incubations were terminated as follows: Metabolic positive control incubations were terminated by adding an equal volume of methanol. All other incubations were terminated by placing the plates on ice. The contents of each well were mixed thoroughly and divided into five cryovials. An equal volume of organic solvent was added to one cryovial. The samples were either immediately analyzed or stored in cryovials at −70°±10 C until analysis.

All samples were analyzed by reverse-phase HPLC. A UV profile of the samples was obtained followed by liquid chromatography-mass spectrometry (LC/MS) analysis using a Micromass® Q-Tof-2 mass spectrometer capable of conducting accurate mass measurement. Preliminary metabolite identification was aided by the use of Metabolynx® software.

The metabolic capacity of the hepatocytes from each species was evaluated by measuring the formation of 7-hydroxycoumarin and its conjugated derivatives, 7-hydroxycoumarin glucuronide and 7-hydroxycoumarin sulfate in the metabolic positive control samples using a validated HPLC bioanalytical method. The cryopreserved hepatocytes used in the study were considered to be metabolically active and the incubations acceptable.

The relative amounts of Androxal and its metabolites after 1 and 4 hour incubations are reported below at Tables 1-4.

Four major Androxal® metabolites (C26H30NO3Cl (M3), C26H28NO2Cl (M14), C27H30NO3Cl (M15) and C24H24NOCl (M22); see Tables 1-4 below) were observed in incubations with human hepatocytes, with hydroxylation, dealkylation and dehydrogenation as the major observed metabolic transformations. Metabolites C24H24NO2Cl, C26H28NO2Cl, C27H30NO3Cl and C24H24NOCl were also observed in incubations with rat, dog and monkey hepatocytes. C26H30NO3Cl was observed in the monkey and dog hepatocyte incubations with the 30 mM Androxal® dose. At the low dose of Androxal®, consistent with blood levels found in clinical trials (3 µM), hydroxylated metabolites predominate (see Tables 3 and 4 below). It was determined that 85% and 91% of all recovered metabolites were hydroxylated compounds at 1 and 4 hours respectively at the low dose (e.g. C26H28NO2Cl). At the higher dose of Androxal® (30 µM) de-ethylation becomes important and about half of all metabolites recovered were deethylated (2x demethylated) compounds (e.g. C24H24NOCl). Without being bound by theory, it is believed that CYP3A4 may have a higher binding constant/lower affinity for trans-clomiphene. Alternatively, higher concentrations of trans-clomiphene may overwhelm the CYP 2D6 system capacity in these hepatocytes. CYP 2D6 is largely responsible for hydroxylation and de-ethylation is accomplished largely through CYP 3A4. This data suggests that the primary active metabolites of trans-clomiphene are 4-OH-trans-clomiphene, produced by the action of CYP 2D6 and N-desethyl-trans-clomiphene, produced by the action of CYP 3A4. Therapeutic administration of these metabolites is expected to ameliorate the disorders described herein while reducing side effects which accompany administration of trans-clomiphene resulting from the individual actions of trans-clomiphene and its metabolite components shown below.

TABLE 1

Metabolite Profile of Incubations Containing 30 µM Androxal ® for 4 hours

| Cmpd | RT | m/z | Transformation | Human | Cyno. monkey | Beagle dog | SD Rat |
|---|---|---|---|---|---|---|---|
| C26H28ClNO (Androxal ®) | 27.6 | 406 | None | 4012.5 | 2828.5 | 4989.3 | 3123.3 |
| C26H29NO4 | 17.7 | 420 | Dechlorination + H + Hydroxylation + 2x Hydroxylation | — | — | — | 130.2 |
| C27H31NO3 | 22.5 | 418 | Methylation + 2x Hydroxylation + Dechlorination + H | 20.3 | 26.6 | — | 438.2 |
| C26H30NO3Cl | 22.7 | 440 | Reduction + 2x Hydroxylation | 125.9 | 64.7 | 65.9 | — |
| C32H36NO8Cl | 22.8 | 598 | Gluc + Hydroxylation | — | — | 16.6 | 29.5 |
| C26H30NO3Cl | 22.95 | 440 | Reduction_2x Hydroxylation | — | — | 43.7 | — |
| C27H30NO3Cl | 22.9 | 452 | Methylation + 2x Hydroxylation | — | — | — | 15.8 |
| C32H36NO8Cl | 23.1 | 598 | Gluc + Hydroxylation | 22.4 | 18.1 | — | 30.8 |
| C26H28NO3Cl | 23.5 | 438 | 2x Hydroxylation | — | — | 86.2 | 117.1 |
| C36H43N4O7SCl | 23.5 | 711 | S-Glutathione conjugation | — | — | — | 15.9 |
| C26H30NO3Cl | 24.0 | 440 | Reduction + 2x Hydroxylation | 66.8 | 53.1 | — | — |
| C36H43N4O7SCl | 24.2 | 711 | S-Glutathione conjugation | — | — | — | 13.6 |
| C27H31NO3 | 24.3 | 418 | Methylation + 2x Hydroxylation + Dechlorination + H | 28 | 37.5 | — | 530.7 |
| C24H24NO2Cl | 24.7 | 394 | Hydroxyl + Deethylation | — | 335.6 | 113.1 | 188.9 |
| C26H28NO2Cl | 25.0 | 422 | Hydroxylation | 747.4 | 724.4 | 1999.3 | 1432.8 |
| C27H30NO3Cl | 25.1 | 452 | Methylation + 2x Hydroxylation | 140.7 | 93.9 | 310.1 | 905.3 |
| C27H30NO6ClS | 25.5 | 532 | Methylation + 2x Hydroxyl + Sulfate conj. | — | — | 152.8 | — |

TABLE 1-continued

Metabolite Profile of Incubations Containing 30 μM Androxal ® for 4 hours

| Cmpd | RT | m/z | Transformation | Human | Cyno. monkey | Beagle dog | SD Rat |
|---|---|---|---|---|---|---|---|
| C26H28NO3Cl | 25.5 | 438 | 2x Hydroxylation | — | — | 82.4 | 70.7 |
| C26H28NO7Cl | 25.6 | 502 | 3 x 2 x Hydroxylation | 68.0 | 44.8 | 64.2 | — |
| C26H28NO2Cl | 25.8 | 422 | Hydroxylation | 53.9 | 63.2 | 30.5 | — |
| C27H30NO3Cl | 25.9 | 452 | Methylation + 2x Hydroxylation | 24.7 | 10.3 | — | 97.4 |
| C24H24NOCl | 27.5 | 378 | 2x Demethylation (Deethylation) | 1262.4 | 2175.0 | 723.5 | 673.8 |
| C26H28NO2Cl | 28.0 | 422 | Hydroxylation | — | — | — | 174.6 |
| C24H24NO2Cl | 29.06 | 394 | Hydroxyl + Deethylation | — | 59.1 | — | — |

Abbreviations:
RT, retention time;
Cyno., cynomolgus;
SD, Sprague-Dawley;
m/z, mass/charge

TABLE 2

Metabolite Profile of Incubations Containing 30 mM Androxal ® for 1 hour

| Cmpd | RT | m/z | Transformation | Human | Cyno. monkey | Beagle dog | SD Rat |
|---|---|---|---|---|---|---|---|
| C26H28ClNO (Androxal ®) | 27.6 | 406 | None | 4297.8 | 3166.4 | 6227.3 | 3166.8 |
| C27H31NO3 | 22.5 | 418 | Methylation + 2x Hydroxylation + Dechlorination + H | 18.1 | 19.3 | — | 346.1 |
| C26H30NO3Cl | 22.7 | 440 | Reduction + 2x Hydroxylation | 56.1 | 43.3 | 117.3 | — |
| C26H28NO3Cl | 23.5 | 438 | 2x Hydroxylation | — | — | 70.0 | 39.8 |
| C26H30NO3Cl | 24.0 | 440 | Reduction + 2x Hydroxylation | 32.9 | 44.9 | — | — |
| C27H31NO3 | 24.3 | 418 | Methylation + 2x Hydroxylation + Dechlorination + H | 30.0 | 28.9 | — | 420.3 |
| C24H24NO2Cl | 24.7 | 394 | Hydroxyl + Deethylation | 22.0 | 54.0 | 36.7 | 45.2 |
| C26H28NO2Cl | 25.0 | 422 | Hydroxylation | 538.8 | 455.5 | 1535.2 | 992.7 |
| C27H30NO3Cl | 25.1 | 452 | Methylation + 2x Hydroxylation | 36.4 | 22.6 | 199.7 | 445.8 |
| C27H30NO6ClS | 25.5 | 532 | Methylation + 2x Hydroxyl + Sulfate conj. | — | — | 24.9 | — |
| C26H28NO3Cl | 25.5 | 438 | 2x Hydroxylation | — | — | 102.2 | 16.2 |
| C26H28NO7Cl | 25.6 | 502 | 3 x 2 x Hydroxylation | — | — | 20.8 | — |
| C26H28NO2Cl | 25.8 | 422 | Hydroxylation | 25.4 | 27.9 | — | — |
| C27H3ONO3Cl | 25.9 | 452 | Methylation + 2x Hydroxylation | — | — | — | 41.7 |
| C24H24NOCl | 27.5 | 378 | 2x Demethylation (Deethylation) | 699.8 | 1029.8 | — | 336.6 |
| C24H24NO2Cl | 29.06 | 394 | Hydroxyl + Deethylation | — | 10.5 | — | — |

Abbreviations:
RT, retention time;
Cyno., cynomolgus;
SD, Sprague-Dawley;
m/z, mass/charge

TABLE 3

Metabolite Profile of Incubations Containing 3 μM Androxal ® for 4 hours

| Cmpd | RT | m/z | Transformation | Human | Cyno. monkey | Beagle dog | SD Rat |
|---|---|---|---|---|---|---|---|
| C26H28ClNO (Androxal ®) | 27.6 | 406 | None | 285.4 | 84.2 | 103.2 | 182.5 |
| C26H30NO3Cl | 22.7 | 440 | Reduction + 2x Hydroxylation | 49.3 | — | — | — |
| C26H28NO3Cl | 23.5 | 438 | 2x Hydroxylation | — | — | 27.9 | — |
| C24H24NO2Cl | 24.7 | 394 | Hydroxyl + Deethylation | 29.4 | — | 14.3 | — |
| C26H28NO2Cl | 25.0 | 422 | Hydroxylation | 247.0 | 43.4 | 103.4 | 31.1 |
| C27H30NO3Cl | 25.1 | 452 | Methylation + 2x Hydroxylation | 148.4 | 41.5 | 256.1 | 134.5 |
| C27H30NO3Cl | 25.5 | 452 | Methylation + 2x Hydroxylation | — | 15.7 | — | — |
| C27H30NO6ClS | 25.5 | 532 | Methylation + 2x Hydroxyl + Sulfate conj. | — | — | 27.5 | — |
| C24H24NOCl | 27.5 | 378 | 2x Demethylation (Deethylation) | 43.4 | — | 18.6 | — |

Abbreviations:
RT, retention time;
Cyno., cynomolgus;
SD, Sprague-Dawley;
m/z, mass/charge

TABLE 4

Metabolite Profile of Incubations Containing 3 μM Androxal ® for 1 Hour

| Cmpd | RT | m/z | Transformation | Human | Cyno. monkey | Beagle dog | SD Rat |
|---|---|---|---|---|---|---|---|
| C26H28ClNO (Androxal ®) | 27.6 | 406 | None | 625.8 | 279.1 | 148.9 | 240.0 |
| C26H29NO4 | 17.7 | 420 | Dechlorination + H + Hydroxylation + 2x Hydroxylation | — | — | — | 36.7 |
| C27H31NO3 | 22.5 | 418 | Methylation + 2x Hydroxylation + Dechlorination + H | — | — | — | 24.2 |
| C26H30NO3Cl | 22.7 | 440 | Reduction + 2x Hydroxylation | 24.5 | — | — | — |
| C26H28NO3Cl | 23.5 | 438 | 2x Hydroxylation | — | — | 52.5 | — |
| C27H31NO3 | 24.3 | 418 | Methylation + 2x Hydroxylation + Dechlorination + H | — | — | — | 27.1 |
| C24H24NO2Cl | 24.7 | 394 | Hydroxyl + Deethylation | — | 13.6 | 12.2 | — |
| C26H28NO2Cl | 25.0 | 422 | Hydroxylation | 240.3 | 239.4 | 218.8 | 100.9 |
| C27H30NO3Cl | 25.1 | 452 | Methylation + 2x Hydroxylation | 34.9 | 107.4 | 232.9 | 255.8 |
| C27H30NO3Cl | 25.4 | 452 | Methylation + 2x Hydroxylation | — | 12.2 | — | — |
| C27H30NO3Cl | 25.9 | 452 | Methylation + 2x Hydroxylation | — | — | — | 16.2 |

TABLE 4-continued

Metabolite Profile of Incubations Containing 3 μM Androxal ® for 1 Hour

| Cmpd | RT | m/z | Transformation | Human | Cyno. monkey | Beagle dog | SD Rat |
|---|---|---|---|---|---|---|---|
| C24H24NOCl | 27.5 | 378 | 2x Demethylation (Deethylation) | 48.3 | 22.3 | 25.9 | — |

Abbreviations:
RT, retention time;
Cyno., cynomolgus;
SD, Sprague-Dawley;
m/z, mass/charge

The invention claimed is:

1. A pharmaceutical composition comprising about 100% w/w of a trans-clomiphene metabolite having a structural formula selected from the group consisting of:

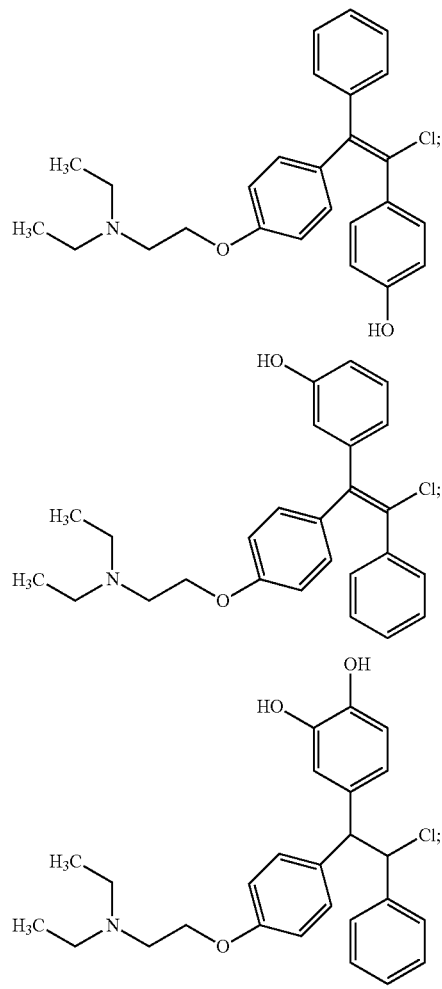

-continued

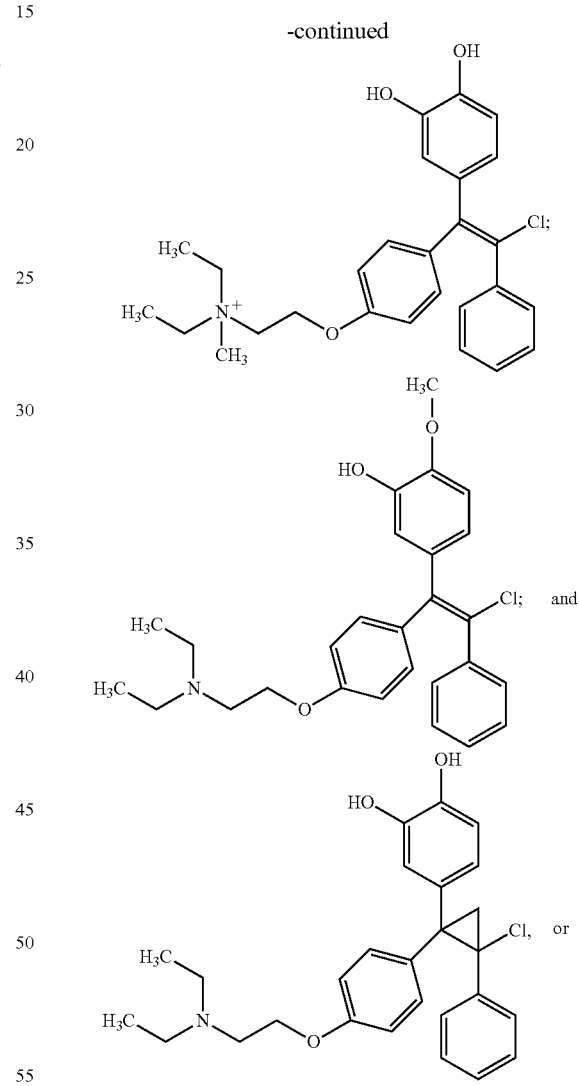

a pharmaceutically acceptable salt thereof as active agent and a pharmaceutically acceptable carrier, wherein the pharmaceutical composition is a capsule or tablet.

* * * * *